US012310992B2

(12) United States Patent
Jeffs et al.

(10) Patent No.: US 12,310,992 B2
(45) Date of Patent: *May 27, 2025

(54) TREATMENT OF PULMONARY ARTERIAL HYPERTENSION WITH PROSTACYCLIN-TREATED ENDOTHELIAL PROGENITOR CELLS

(71) Applicant: United Therapeutics Corporation, Silver Spring, MD (US)

(72) Inventors: Roger Jeffs, Chapel Hill, NC (US); Thomas Petersen, Durham, NC (US); Roger M. Ilagan, Burlington, NC (US); Michael Wade, Chapel Hill, NC (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/535,745

(22) Filed: Dec. 11, 2023

(65) Prior Publication Data

US 2024/0131078 A1 Apr. 25, 2024

Related U.S. Application Data

(60) Division of application No. 17/072,430, filed on Oct. 16, 2020, now Pat. No. 11,839,631, which is a continuation of application No. 16/002,250, filed on Jun. 7, 2018, now Pat. No. 10,842,823, which is a division of application No. 14/418,557, filed as application No. PCT/US2013/052700 on Jul. 30, 2013, now Pat. No. 10,016,463.

(60) Provisional application No. 61/750,458, filed on Jan. 9, 2013, provisional application No. 61/678,208, filed on Aug. 1, 2012.

(51) Int. Cl.
| | |
|---|---|
| *A61K 35/44* | (2015.01) |
| *A61K 31/5585* | (2006.01) |
| *A61K 35/02* | (2015.01) |
| *A61K 35/28* | (2015.01) |
| *A61K 45/06* | (2006.01) |
| *C12N 5/071* | (2010.01) |

(52) U.S. Cl.
CPC .......... *A61K 35/44* (2013.01); *A61K 31/5585* (2013.01); *A61K 35/02* (2013.01); *A61K 35/28* (2013.01); *A61K 45/06* (2013.01); *C12N 5/0692* (2013.01); *C12N 2501/999* (2013.01); *F04C 2270/041* (2013.01)

(58) Field of Classification Search
None
See application file for complete search history.

(56) References Cited

U.S. PATENT DOCUMENTS

| | | | |
|---|---|---|---|
| 3,089,815 A | 5/1963 | Lieb et al. | |
| 4,352,883 A | 10/1982 | Lim | |
| 4,353,888 A | 10/1982 | Sefton | |
| 4,714,680 A | 12/1987 | Civin | |
| 4,965,204 A | 10/1990 | Civin | |
| 4,968,733 A | 11/1990 | Mueller et al. | |
| 4,976,859 A | 12/1990 | Wechs | |
| 4,983,393 A | 1/1991 | Cohen et al. | |
| 5,026,365 A | 6/1991 | Rossini et al. | |
| 5,035,994 A | 7/1991 | Civin | |
| 5,071,741 A | 12/1991 | Brockbank | |
| 5,084,350 A | 1/1992 | Chang et al. | |
| 5,130,144 A | 7/1992 | Civin | |
| 5,137,809 A | 8/1992 | Loken et al. | |
| 5,158,881 A | 10/1992 | Aebischer et al. | |
| 5,284,761 A | 2/1994 | Aebischer et al. | |
| 5,643,192 A | 7/1997 | Hirsh et al. | |
| 5,651,982 A | 7/1997 | Marx | |
| 5,691,176 A | 11/1997 | Lebkowski et al. | |
| 5,693,531 A | 12/1997 | Chiorini et al. | |
| 5,750,397 A | 5/1998 | Tsukamoto et al. | |
| 5,800,828 A | 9/1998 | Dionne et al. | |
| 5,811,094 A | 9/1998 | Caplan et al. | |
| 6,387,369 B1 | 5/2002 | Pittenger et al. | |
| 6,468,527 B2 | 10/2002 | Austin et al. | |
| 7,638,128 B2 | 12/2009 | Dzau et al. | |
| 10,016,463 B2* | 7/2018 | Jeffs | A61P 9/14 |
| 10,080,730 B2* | 9/2018 | Jeffs | A61K 35/28 |
| 10,842,823 B2* | 11/2020 | Jeffs | A61P 9/12 |
| 11,141,393 B2* | 10/2021 | Jeffs | A61P 43/00 |
| 11,839,631 B2* | 12/2023 | Jeffs | A61K 31/5585 |
| 2003/0118567 A1 | 6/2003 | Stewart | |
| 2005/0165111 A1 | 7/2005 | Wade et al. | |

(Continued)

FOREIGN PATENT DOCUMENTS

| | | |
|---|---|---|
| WO | WO 92/04033 A1 | 3/1992 |
| WO | WO 92/19195 A1 | 11/1992 |

(Continued)

OTHER PUBLICATIONS

"Second European Consensus Document on Chronic Critical Leg Ischemia", Circulation, Nov. 1991, 84(4 Suppl.):IV-1-IV-26.
Abisambra et al., "Abstracts for the 19th Annual Meeting of the American Society for Neural Therapy and Repair," Cell Transplantation, 2012, 21:773-797.
Actelion Pharmaceuticals, "VELETRI: epoprostenol," prescribing information, 2011, 4 pages.
Aizman et al., "Extracellular Matrix Produced by Bone Marrow Stromal Cells and by Their Derivative, SB623 Cells, Supports Neural Cell Growth," Journal of Neuroscience Research, 2009, 87:3198-3206.

(Continued)

Primary Examiner — Blaine Lankford
(74) Attorney, Agent, or Firm — Foley & Lardner LLP

(57) ABSTRACT

The current application is directed to a method for treating pulmonary arterial hypertension (PAH), comprising: providing isolated endothelial progenitor cells (EPCs); treating the EPCs with prostacyclin, wherein the treated EPCs exhibit a hyperproliferative phenotype with enhanced angiogenic property; and administering a composition comprising the treated EPCs into a subject suffering from PAH.

12 Claims, No Drawings

(56) References Cited

U.S. PATENT DOCUMENTS

| | | |
|---|---|---|
| 2007/0065414 A1 | 3/2007 | Freyman et al. |
| 2008/0050349 A1 | 2/2008 | Stewart |
| 2008/0226595 A1 | 9/2008 | Edinger et al. |
| 2009/0177262 A1 | 7/2009 | Oberti et al. |
| 2009/0274665 A1 | 11/2009 | Akabutu et al. |
| 2010/0040584 A1 | 2/2010 | Melero-Martin et al. |
| 2011/0003008 A1 | 1/2011 | Lim |
| 2012/0172970 A1 | 7/2012 | Cottone, Jr. et al. |
| 2014/0193379 A1 | 7/2014 | Jeffs et al. |
| 2014/0234278 A1 | 8/2014 | Heffner |
| 2015/0246078 A1 | 9/2015 | Jeffs et al. |
| 2018/0110807 A1 | 4/2018 | Ilagan et al. |

FOREIGN PATENT DOCUMENTS

| | | | |
|---|---|---|---|
| WO | WO 93/14191 A1 | 7/1993 | |
| WO | WO 94/29438 A1 | 12/1994 | |
| WO | WO 95/05452 A1 | 2/1995 | |
| WO | WO 95/07611 A1 | 3/1995 | |
| WO | WO 95/27071 A1 | 10/1995 | |
| WO | WO 96/27287 A1 | 9/1996 | |
| WO | WO 96/29862 A1 | 10/1996 | |
| WO | WO 97/21824 A1 | 6/1997 | |
| WO | WO 97/21825 A1 | 6/1997 | |
| WO | WO 98/14058 A1 | 4/1998 | |
| WO | WO 2000/024897 A1 | 5/2000 | |
| WO | WO 01/04268 A1 | 1/2001 | |
| WO | WO 2004/050180 A2 | 6/2004 | |
| WO | WO 2004/084921 A1 | 10/2004 | |
| WO | WO 2004/085630 A1 | 10/2004 | |
| WO | WO 2006/032092 A1 | 3/2006 | |
| WO | WO 2009/057313 A1 | 5/2009 | |
| WO | WO 2012/027740 A1 | 3/2012 | |

OTHER PUBLICATIONS

Allen et al., "Type I collagen, fibrin and PuraMatrix matrices provide permissive environments for human endothelial and mesenchymal progenitor cells to form neovascular networks," Journal of Tissue Engineering and Regenerative Medicine, 2011, 5:e74-e86.

Asahara et al., "Isolation of Putative Progenitor Endothelial Cells for Angiogenesis," Science, Feb. 17, 1997, 275:964-967.

Assmus et al., "Transplantation of Progenitor Cells and Regeneration Enhancement in Acute Myocardial Infarction (TOPCARE-AMI)," Circulation, Nov. 11, 2002, 106:3009-3017.

Barst, Robyn MD, FACC, "Is it Possible to Reverse the Endothelial Dysfunction in Pulmonary Arterial Hypertension?", Journal of the American College of Cardiology, 2007, 49(14):1572-1574.

Bregni et al., "Human Peripheral Blood Hematopoietic Progenitors Are Optimal Targets of Retroviral-Mediated Gene Transfer," Blood, Sep. 15, 1992, 80(6):1418-1422.

Chen et al., "Effect on Left Ventricular Function of Intracoronary Transplantation of Autologous Bone Marrow Mesenchymal Stem Cell in Patients with Acute Myocardial Infarction," The American Journal of Cardiology, Jul. 1, 2004, 94:92-95.

Clinical All-Round, Nov. 2009, 58(11):2324-2337.

Coffin et al., Eds. "Retroviruses", Chapter 9 pp. 437-473, Cold Springs Harbor Laboratory Press, 1997.

D'Alonzo et al., "Survival in Patients with Primary Pulmonary Hypertension," Ann. Intern. Med., Sep. 1, 1991, 115(5):343-349.

Das et al., "The Role of Hypoxia in Bone Marrow-Derived Mesenchymal Stem Cells: Considerations for Regenerative Medicine Approaches," Tissue Engineering: Part B, Apr. 1, 2010, 16(2):159-168.

Di Stefano et al., "The prostacyclin analogue iloprost increases circulating endothelial progenitor cells in patients with critical limb ischemia," Thrombosis and Haemostasis, Oct. 13, 2008, 100(5):871-877.

Doyle et al., "Endothelial Progenitor Cells," Endothelium, 2006, 13(6):403-410.

Eells et al., "Advances in Prostacyclin Therapy for Pulmonary Arterial Hypertension," Critical Care Nurse, Apr. 2004, 24(2):42-54.

Eneroth et al., "Amputation for occlusive arterial disease, A prospective multicentre study of 177 amputees," Int. Orthop. (SICOT), 1992, 16:383-387.

Flamme et al., "Induction of vasculogenesis and hematopoiesis in vitro," Development, 1992, 116(2):435-439.

Grant et al., "Iloprost: A Review of its Pharmacodynamic and Pharmacokinetic Properties, and Therapeutic Potential in Peripheral Vascular Disease, Myocardial Ischaemia and Extracorporeal Circulation Procedures," Drugs, 1992, 43(6):889-924.

Gruber, Scott A., "The Case for Local Immunosuppression," Transplantation, Jul. 1992, 54:1-11.

Hall et al., "Endothelin receptor expression in idiopathic pulmonary arterial hypertension: effect of bosentan and epoprostenol treatment," Eur. Respir. J., 2011, 38:851-860.

Hatzopoulos et al., "Isolation and characterization of endothelial progenitor cells from mouse embryos," Development, 1998, 125(8):1457-1468.

He et al., "Angiogenic function of prostacyclin biosynthesis in human endothelial progenitor cells," Circulation Research, Jul. 3, 2008, 103(1):80-88.

Hill et al, "Circulating Endothelial Progenitor Cells, Vascular Function, and Cardiovascular Risk," N. Engl. J. Med., 2003, 348:593-600.

Hu et al., "Exosomal miRNAs: biological properties and therapeutic potential," Frontiers in Genetics, Apr. 20, 2012, 3(56):1-9.

Humbert et al., "Cellular and Molecular Pathobiology of Pulmonary Arterial Hypertension," J. Am. Coll. Cardiol., 2004, 43(12:SupplS):13S-24S.

Ingram et al., "Identification of a novel hierarchy of endothelial progenitor cells using human peripheral and umbilical cord blood," Blood, Jun. 29, 2004, 104:2752-2760.

Ishii et al., "Mesenchymal stem cell-based gene therapy with prostacyclin synthase enhanced neovascularization in hindlimb ischemia," Atherosclerosis, 2009, 206:109-118.

Isner et al., "Angiogenesis and vasculogenesis as therapeutic strategies for postnatal neovascularization," J. Clin. Invest., May 1999, 103(9):1231-1236.

Kalka et al., "Transplantation of ex vivo expanded endothelial progenitor cells for therapeutic neovascularization," P.N.A.S., Mar. 29, 2000, 97(7):3422-3427.

Kamio et al., "Prostacyclin analogs stimulate VEGF production from human lung fibroblasts in culture," Am. J. Physiol. Lung Cell. Mol. Physiol., 2008, 294:L1226-L1232.

Karlsson et al., "Nucleation and Growth of Ice Crystals Inside Cultured Hepatocytes During Freezing in the Presence of Dimethyl Sulfoxide," Biophysical J., Dec. 1993, 65:2524-2536.

Kawabe et al., "Role of Autocrine Prostacyclin System in Crucial Functions of Endothelial Progenitor Cells," Circ. J., 2008, 72(Suppl. 1):503, PE-570.

Kawabe, Junichi, "Q&A about Thrombosis (Part 6): Please explain prostacyclin and revascularization," Thrombosis and Circulation, 2011, 19(1):189-191.

Keeley et al., "Fibrocytes: Bringing new insights into mechanisms of inflammation and fibrosis," Int. J. Biochem. Cell Biol., 2010, 42:535-542.

Lai et al., "Exosome secreted by MSC reduces myocardial ischemia/reperfusion injury," Stem Cell Research, 2010, 4(3):214-222.

Lai et al., "Mesenchymal stem cell exosome: a novel stem cell-based therapy for cardiovascular disease," Regen. Med., 2011, 6(4):481-492.

Lau et al., "Stem Cells and Regenerative Medicine in Lung Biology and Diseases," Molecular Therapy, Mar. 6, 2012, 20(6):1116-1130.

Lee et al., "Exosomes Mediate the Cytoprotective Action of Mesenchymal Stromal Cells on Hypoxia-Induced Pulmonary Hypertension," Circulation, Oct. 31, 2012, 126(22):2601-2611.

Liu et al., "Engineered Endothelial Progenitor Cells That Overexpress Prostacyclin Protect Vascular Cells," Journal of Cellular Physiology, Mar. 20, 2012, 227(7):2907-2916.

Mayer et al., "Vascular Endothelial Growth Factor (VEGF-A) Expression in Human Mesenchymal Stem Cells: Autocrine and

(56) References Cited

OTHER PUBLICATIONS

Paracrine Role on Osteoblastic and Endothelial Differentiation," Journal of Cellular Biochemistry, Jul. 1, 2005, 95(4):827-839.

Murohara et al., "Transplanted cord blood-derived endothelial precursor cells augment postnatal neovascularization," J. Clin. Invest., Jun. 2000, 105(11):1527-1536.

Nagaya et al., "Hybrid Cell-Gene Therapy for Pulmonary Hypertension Based on Phagocytosing Action of Endothelial Progenitor Cells," Circulation, Jun. 30, 2003, 108:889-895.

Ribatti, Domenico, "The discovery of endothelial progenitor cells, An historical review," Leukemia Research, 2007, 31:439-444.

Risau et al., "Vasculogenesis and angiogenesis in embryonic-stem-cell-derived embryoid bodies," Development, 1988, 102(3):471-478.

Risau, Werner, "Differentiation of endothelium," FASEB J., 1995, 9(10):926-933.

Risau, Werner, "Mechanisms of angiogenesis," Nature, Apr. 17, 1997, 386(6626): 671-674.

Rissanen et al., "Gene therapy for therapeutic angiogenesis in critically ischaemic lower limb—on the way to the clinic," European Journal of Clinical Investigation, 2001, 31:651-666.

Ruan et al., "Prostacyclin Therapy for Pulmonary Arterial Hypertension," Texas Heart Institute Journal, 2010, 37(4):391-399.

Sahara, Makoto, Clinic All-Round, 2009, 58(11):2324-2336, with English translation of indicated relevant portions.

Shantsila et al., "Endothelial Progenitor Cells in Cardiovascular Disorders," Journal of the American College of Cardiology, 2007, 49(7):741-752.

Shintani, Satoshi, Heart View, 2011, 15(8):90-96, with English translation of indicated relevant portions.

Smadja et al., "Treprostinil increases the number and angiogenic potential of endothelial progenitor cells in children with pulmonary hypertension," Angiogenesis, 2011, 14(1):17-27.

Smithies et al., "Insertion of DNA sequences into the human chromosomal Beta-globin locus by homologous recombination," Nature, Sep. 19, 1985, 317:230-234.

Takahashi et al., "Ischemia- and cytokine-induced mobilization of bone marrow-derived endothelial progenitor cells for neovascularization," Nature Medicine, Apr. 1999, 5(4):434-438.

Topol et al., "Combined Tissue-Type Plasminogen Activator and Prostacyclin Therapy for Acute Myocardial Infarction," J. Am. Coll. Cardiol., 1989, 14(4):877-884.

Tyrrell et al., "Critical leg ischaemia: an appraisal of clinical definitions," Br. J. Surg., Feb. 1003, 80:177-180.

Umar et al., "Novel Approaches to Treat Experimental Pulmonary Arterial Hypertension: A Review," Journal of Biomedicine and Biotechnology, Jan. 1, 2010, 8(1):1-11, Article ID 702836.

Wang et al., "Transplantation of Autologous Endothelial Progenitor Cells May Be Beneficial in Patients With Idiopathic Pulmonary Arterial Hypertension," J. Am. Coll. Cardiol., 2007, 49(14):1566-1571.

Williams et al., "Mesenchymal Stem Cells: Biology, Pathophysiology, Translational Findings, and Therapeutic Implications for Cardiac Disease," Circ. Res., 2011, 109:923-940.

Yoder et al., "Redefining endothelial progenitor cells via clonal analysis and hematopoietic stem/progenitor cell principals," Blood, 2007, 109:1801-1809.

Zhao et al., "Rescue of Monocrotaline-Induced Pulmonary Arterial Hypertension Using Bone Marrow- Derived Endothelial-Like Progenitor Cells," Circ. Res., 2006, 96:442-450.

Zhen et al., "Mesenchymal stem cell transplantation increases expression of vascular endothelial growth factor in papain-induced emphysematous lungs and inhibits apoptosis of lung cells," Cytotherapy, Sep. 1, 2010, 12(5):605-614.

Zheng et al., "Fidelity of targeted recombination in human fibroblasts and murine embryonic stem cells," Proc. Natl. Acad. Sci. USA, Sep. 1991, 88:8067-8071.

\* cited by examiner

TREATMENT OF PULMONARY ARTERIAL HYPERTENSION WITH PROSTACYCLIN-TREATED ENDOTHELIAL PROGENITOR CELLS

CROSS-REFERENCE TO RELATED APPLICATIONS

This application is a Divisional of U.S. application Ser. No. 17/072,430, filed Oct. 16, 2020, which is a Continuation of U.S. application Ser. No. 16/002,250, filed Jun. 7, 2018, which is a Divisional of U.S. application Ser. No. 14/418,557, which is the U.S. National Stage of PCT/US2013/052700, filed Jul. 30, 2013, which claims the benefit of U.S. Provisional Application No. 61/678,208, filed on Aug. 1, 2012, and U.S. Provisional Application No. 61/750,458, filed on Jan. 9, 2013, the contents of which are hereby incorporated by reference in their entireties.

BACKGROUND OF THE INVENTION

The present application relates to the use of endothelial progenitor cells (EPCs) in treating pulmonary arterial hypertension (PAH) and other types of pulmonary hypertension.

Pulmonary arterial hypertension is a progressive lung disorder which, untreated, leads to death on average within 2.8 years after being diagnosed. An increasing constriction of the pulmonary circulation leads to increased stress on the right heart, which may develop into right heart failure. By definition, the mean pulmonary arterial pressure (mPAP) in a case of chronic pulmonary hypertension is >25 mmHg at rest or >30 mmHg during exertion (normal value <20 mmHg). The pathophysiology of pulmonary arterial hypertension is characterized by vasoconstriction and remodeling of the pulmonary vessels. In chronic PAH there is neomuscularization of initially unmuscularized pulmonary vessels, and the vascular muscles of the already muscularized vessels increase in circumference. This increasing obliteration of the pulmonary circulation results in progressive stress on the right heart, which leads to a reduced output from the right heart and eventually ends in right heart failure (M. Humbert et al., J. Am. Coll. Cardiol. 2004, 43, 13S-24S). PAH is an extremely rare disorder, with a prevalence of 1-2 per million. The average age of the patients has been estimated to be 36 years, and only 10% of the patients were over 60 years of age. Distinctly more women than men are affected (G. E. D'Alonzo et al., Ann. Intern. Med. 1991, 115, 343-349).

Standard therapies available on the market (e.g. prostacyclin analogs, endothelin receptor antagonists, phosphodiesterase inhibitors) are able to improve the quality of life, the exercise tolerance and the prognosis of the patients. The principles of these therapies are primarily hemodynamic, influencing vessel tone but having no direct influence on the pathogenic remodeling processes. In addition, the possibility of using these medicaments is restricted through the sometimes serious side effects and/or complicated types of administration. The period over which the clinical situation of the patients can be improved or stabilized by specific monotherapy is limited. Eventually the therapy escalates and thus a combination therapy is applied, where a plurality of medicaments must be given concurrently. Despite all the advances in the therapy of pulmonary arterial hypertension there is as yet no prospect of cure of this serious disorder.

Endothelial progenitor cells have been identified in adult bone marrow as well as in peripheral blood and human umbilical cord blood, and have been shown to maintain their potency to proliferate and to differentiate into mature endothelial cells (Ashara et al., Science 275:964 (1997); Murohara et al., J. Clin. Invest. 105(11):1527-36(2000)). Vasculogenesis, the development of new blood vessels during embryogenesis begins with the formation of blood islands comprising endothelial progenitor cells (EPCs) and hematopoietic stem cells (Risau, Nature 386(6626):671-4 (1997); Risau, FASEB J. 9(10):926-33 (1995); Risau et al., Development 102(3):471-8 (1988); Flamme et al., Development 116(2):435-9 (1992); Hatzopoulos et al., Development 125(8):1457-68 (1998); Doyle et al., Endothelium 13(6):403-10 (2006); Ribatti, Leuk Res. (4):439-44 (2007)).

EPCs have been shown to participate in postnatal neovascularization (Takahashi et al., Nat Med. 5(4):434-8 (1999); Isner and Asahara, J Clin Invest. 103(9):1231-6 (1999)). Furthermore, EPCs were found to participate in angiogenesis, vascular repair and vasculoprotection (Doyle et al., Endothelium 13(6):403-10 (2006)).

It has now been surprisingly found that prostacyclin-treated EPCs are useful in treating PAH.

SUMMARY OF THE INVENTION

One embodiment of the current invention is a method for treating pulmonary arterial hypertension (PAH), comprising: providing isolated endothelial progenitor cells (EPCs); treating the EPCs with prostacyclin, wherein the treated EPCs exhibit a hyperproliferative phenotype with enhanced angiogenic activity, and administering a composition comprising the treated EPCs to a subject suffering from PAH. In another embodiment, the prostacyclin may be selected from the group consisting of epoprostenol sodium, treprostinil, ilprost, and $PGI_2$ receptor agonist. In another embodiment, the subject is a human being. In another embodiment, the EPCs are autologous, are isolated from the blood of the subject suffering from PAH, are endothelial colony forming cells, are genetically modified, are co-administered with at least one growth factor, are co-administered with mesenchymal stem cells or a culture medium that has been in contact with mesenchymal stem cells and contains one or more components thereof, and/or are co-administered with prostacyclin. In another embodiment, the EPCs are co-administered with both prostacyclin, and mesenchymal stem cells or a culture medium that has been in contact with mesenchymal stem cells and contains one or more components thereof. In another embodiment, the growth factor is selected from the group consisting of FGF, VEGF-A, VEGF-B, BMP-4, and TGF-Beta. In another embodiment the composition is a pharmaceutical composition further comprising at least on pharmaceutically-acceptable carrier or at least one therapeutic agent other than EPCs. In another embodiment, the composition promotes pulmonary vascular repair. In another embodiment, the subjected is pretreated with prostacyclin before the isolation of the EPCs.

Another embodiment of the current invention is a method for promoting the growth of EPC, comprising: providing isolated EPCs; treating the EPCs with prostacyclin, wherein the prostacyclin enhances the growth of the EPCs. The EPCs may be isolated from a human being or from a tissue or cell culture. In addition, the treated EPCs may exhibit a hyperproliferative phenotype with enhanced angiogenic property. In another embodiment, the prostacyclin is Treprostinil.

Another embodiment of the current invention is a method for treating PAH, comprising: providing isolated EPCs; and co-administering prostacyclin and the EPCs into a subject suffering from PAH.

Another embodiment of the current invention is a method for treating PAH, comprising: providing isolated EPCs;

administering the EPCs into a subject suffering from PAH; and administering prostacyclin into the subject.

Another embodiment of the current invention is a method for treating PAH, comprising: providing isolated EPCs; administering prostacyclin into the subject suffering from PAH; and administering the EPCs into the subject.

DETAILED DESCRIPTIONS

Unless otherwise specified, "a" or "an" means "one or more."

Unless specifically defined otherwise, all technical and scientific terms used herein shall be taken to have the same meaning as commonly understood by one of ordinary skill in the art (e.g., in stem cell biology, cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

As used herein, the term "subject" (also referred to herein as a "patient") includes warm-blooded animals, preferably mammals, including humans. In a preferred embodiment, the subject is a primate. In an even more preferred embodiment, the subject is a human.

As used herein the terms "treating", "treat" or "treatment" include administering a therapeutically effective amount of cells as defined herein sufficient to reduce or eliminate at least one symptom of pulmonary arterial hypertension.

As used herein the terms "preventing", "prevent" or "prevention" include administering a therapeutically effective amount of cells as defined herein sufficient to stop or hinder the development of at least one symptom of pulmonary arterial hypertension.

As used herein, the term "stem cell" refers to self-renewing cells that are capable of giving rise to phenotypically and genotypically identical daughters as well as at least one other final cell type (e.g., terminally differentiated cells). The term "stem cells" includes totipotential, pluripotential and multipotential cells, as well as progenitor and/or precursor cells derived from the differentiation thereof.

As used herein, the term "totipotent cell" or "totipotential cell" refers to a cell that is able to form a complete embryo (e.g., a blastocyst).

As used herein, the term "pluripotent cell" or "pluripotential cell" refers to a cell that has complete differentiation versatility, i.e., the capacity to grow into any of the mammalian body's approximately 260 cell types. A pluripotent cell can be self-renewing, and can remain dormant or quiescent within a tissue.

By "multipotential cell" or "multipotent cell" we mean a cell which is capable of giving rise to any of several mature cell types. As used herein, this phrase encompasses adult or embryonic stem cells and progenitor cells, and multipotential progeny of these cells. Unlike a pluripotent cell, a multipotent cell does not have the capacity to form all of the cell types.

As used herein, the term "progenitor cell" refers to a cell that is committed to differentiate into a specific type of cell or to form a specific type of tissue.

Endothelial Progenitor Cells

The invention provides EPCs. An EPC is an undifferentiated cell that can be induced to proliferate. EPCs are capable of self-maintenance, such that with each cell division, at least one daughter cell will also be an EPC cell. EPCs are capable of being expanded 100, 250, 500, 1000, 2000, 3000, 4000, 5000 or more fold.

Phenotyping of EPCs reveals that these cells express the committed hematopoietic marker CD45. Additionally, an EPC may be immunoreactive for VEGFR-2 and/or Tie-2. Optionally, the EPC is immunoreactive for CD14. The EPC is a multipotent progenitor cell.

Vascular endothelial growth factor (VEGF) acts through specific tyrosine kinase receptors that includes VEGFR-1 (flt-1) and VEGFR-2 (flk-1/KDR) and VEGFR-3/Flt-4 which convey signals that are essential for embryonic angiogenesis and hematopoiesis. While VEGF binds to all three receptors, most biological functions are mediated via VEGFR-2 and the role of VEGFR-1 is currently unknown. VEGFR3/Flt4 signaling is known to be important for the development of lymphatic endothelial cells and VEGFR3 signaling may confer lymphatic endothelial-like phenotypes to endothelial cells. VEGFRs relay signals for processes essential in stimulation of vessel growth, vasorelaxation, induction of vascular permeability, endothelial cell migration, proliferation and survival. Endothelial cells express all different VEGF-Rs. During embryogenesis, it has been reported that a single progenitor cell, the hemangioblast can give rise to both the hematopoietic and vascular systems.

Tie-2 is an endothelial-specific receptor tyrosine kinase and a receptor for angiopoietin 1. It is a type I membrane protein that is expressed predominantly in the endothelium of actively growing blood vessels and may represent the earliest mammalian endothelial cell lineage marker. Tie-2 is likely involved in the regulation of endothelial cell proliferation and differentiation and may direct the special orientation of endothelial cells during the formation of blood vessels.

The CD14 antigen is a high affinity receptor for the complex of lipopolysaccharides (LPS) and LPS-Binding protein (LBP). The CD14 antigen is part of the functional heteromeric LPS receptor complex comprised of CD14, TLR4 and MD-2. CD14 is strongly expressed on most human monocytes and macrophages in peripheral blood, other body fluids and various tissues, such as lymph nodes and spleen. CD14 is weakly expressed on subpopulations of human neutrophils and myeloid dendritic cells.

The CD45 antigen is a tyrosine phosphatase, also known as the leukocyte common antigen (LCA). CD45 is present on all human cells of hematopoietic origin, except erythroid cells, platelets and their precursor cells. The CD45 molecule is required for T cell and B cell activation and is expressed in at least 5 isoforms, depending on the activation status of the cell.

VEGFR-1+, VEGFR-2+ and Tie-2+ cells constituted approximately 3.0.+−0.0.2%, 0.8.+−0.0.5%, 2.0.+−0.0.3% of the total population of mononuclear cells in blood respectively. CD14+/VEGFR-2+ cells constituted approximately 2.0.+–0.0.5% of the total population of monocytes and 0.08.+–0.0.04% of mononuclear cells in blood.

EPCs can be maintained in vitro in long-term cultures. The EPCs are capable of being passed in culture 2, 3, 4, 5, 6, 7, 8, 9, 10, 11, 12 or more times.

EPCs comprise endothelial colony-forming cells, typically developed after 1-3 weeks of cell culture. Endothelial colony-forming cells have the characteristics of precursor cells committed to the endothelial lineage and are capable of merging into neovessels, according to Smardja et al., Angiogenesis 14(1):17-27 (2011).

Isolation & Culture of EPCs

The isolation, purification, ex vivo culturing and characterizing of EPCs are described in Hill et al, N. Engl. J. Med. 348:593-600 (2003), Assmus et al., Circulation 106:3009-16 (2002), Wang et al., J. Am. Coll. Cardiol. 49:1566-71 (2007), and Kalka et al., P.N.A.S. 97:3422-7 (2000), the content of which are hereby incorporated by reference in their entireties. Further, the isolation, purification, ex vivo culturing and characterizing of endothelial colony-forming cells are described in Yoder et al., Blood 109:1801-1809 (2007), Ingram et al., Blood 104:2752-2760 (2004), and Smardja et al., Angiogenesis 14(1):17-27 (2011), the content of which are hereby incorporated by reference in their entireties.

For example, the population of cells are isolated by means of positive selection, or by a mixture of both positive and negative selection in either order. The population of progenitor cells is purified. A purified population of EPCs contains a significantly higher proportion of EPCs than the crude population of cells from which the cells are isolated.

For example, the purification procedure should lead at least to a five fold increase, preferably at least a ten fold increase, more preferably at least a fifteen fold increase, most preferably at least a twenty fold increase, and optimally at least a twenty-five fold increase in EPCs with respect to the total population. The purified population of EPC should include at least 15%, preferably at least 20%, more preferably at least 25%, most preferably at least 35%, and optimally at least 50% of EPCs.

The methods described herein can lead to mixtures comprising up to 75%, preferably up to 80%, more preferably up to 85%, most preferably up to 90% and optimally up to 95% of stem cells. Such methods are capable of producing mixtures comprising 99%, 99.90% and even 100% of EPCs. Accordingly, the purified populations of the invention contain significantly higher levels of EPCs than those that exist in nature, as described above.

The purified population of EPCs can be isolated by contacting a crude mixture of cells containing a population of stem cells that express an antigen characteristic of the EPCs with a molecule that binds specifically to the extracellular portion of the antigen. Such a technique is known as positive selection. The binding of the EPCs to the molecule permit the EPCs to be sufficiently distinguished from contaminating cells that do not express the antigen to permit isolating the stem cells from the contaminating cells. The antigen is preferably VEGFR, and more preferably VEGFR-2.

The molecule used to separate progenitor cells from the contaminating cells can be any molecule that binds specifically to the antigen that characterizes the EPCs. The molecule can be, for example, a monoclonal antibody, a fragment of a monoclonal antibody, or, in the case of an antigen that is a receptor, the ligand of that receptor. For example, in the case of a VEGF receptor, such as FLK-1, the ligand is VEGF.

The unique isolated cells of the present invention can be separated from other cells by virtue of their CD45+ state and possession of vascular endothelial growth factor receptors (VEGFR), e.g. VEGFR-2. The cells can be isolated by conventional techniques for separating cells, such as those described in Civin, U.S. Pat. Nos. 4,714,680, 4,965,204, 5,035,994, and 5,130,144, Tsukamoto et al U.S. Pat. No. 5,750,397, and Loken et al, U.S. Pat. No. 5,137,809, each of which are hereby incorporated by reference in their entireties. Thus, for example, a CD45 specific monoclonal antibody or a VEGFR-specific antibody can be immobilized on a solid support such as nitrocellulose, agarose beads, polystyrene beads, hollow fiber membranes, magnetic beads, and plastic petri dishes. The entire cell population is then be passed through the solid support or added to the beads.

Cells that are bound to the binding molecule can be removed from the cell suspension by physically separating the solid support from the remaining cell suspension. For example, the unbound cells may be eluted or washed away with physiologic buffer after allowing sufficient time for the solid support to bind the stem cells.

The bound cells can be separated from the solid phase by any appropriate method, depending mainly upon the nature of the solid phase and the binding molecule. For example, bound cells can be eluted from a plastic petri dish by vigorous agitation. Alternatively, bound cells can be eluted by enzymatically "nicking" or digesting an enzyme-sensitive "spacer" sequence between the solid phase and an antibody. Suitable spacer sequences bound to agarose beads are commercially available from, for example, Pharmacia.

The eluted, enriched fraction of cells may then be washed with a buffer by centrifugation and preserved in a viable state at low temperatures for later use according to conventional technology. The cells may also be used immediately, for example by being infused intravenously into a recipient.

Those which remain attached to the solid support are those cells which contain a marker which is recognized by the antibody used. Thus, if the anti-CD45 antibody is used, then the resulting population will be greatly enriched in CD45+ cells. If the antibody used is VFGFR, then the resulting population will be greatly enriched in VEGFR+ cells. That population may then be enriched in the other marker by repeating the steps using a solid phase having attached thereto an antibody to the other marker.

Another way to sort CD45+ VEGFR+ cells is by means of flow cytometry, most preferably by means of a fluorescence-activated cell sorter (FACS), such as those manufactured by Becton-Dickinson under the names FACScan or FACSCalibur. By means of this technique, the cells having a CD45 marker thereon are tagged with a particular fluorescent dye by means of an anti-CD45 antibody which has been conjugated to such a dye. Similarly, the VEGFR marker of the cells are tagged with a different fluorescent dye by means of an anti-VEGFR antibody which is conjugated to the other dye. When the stained cells are placed on the instrument, a stream of cells is directed through an argon laser beam that excites the fluorochrome to emit light. This emitted light is detected by a photo-multiplier tube (PMT) specific for the emission wavelength of the fluorochrome by virtue of a set of optical filters. The signal detected by the PMT is amplified in its own channel and displayed by a computer in a variety of different forms—e.g., a histogram, dot display, or contour display. Thus, fluorescent cells which emit at one wavelength, express a molecule that is reactive with the specific fluorochrome-labeled reagent, whereas non-fluorescent cells or fluorescent cells which emit at a different wavelength do not express this molecule but may express the molecule which is reactive with the fluorochrome-labeled reagent which fluoresces at the other wavelength. The flow cytometer is also semi-quantitative in that it displays the amount of fluorescence (fluorescence intensity) expressed by the cell. This correlates, in a relative sense, to the number of the molecules expressed by the cell.

Flow cytometers can also be equipped to measure non-fluorescent parameters, such as cell volume or light scattered by the cell as it passes through the laser beam. Cell volume is usually a direct measurement. The light scatter PMTs detect light scattered by the cell either in a forward angle (forward scatter; FSC) or at a right angle (side scatter; SSC). FSC is usually an index of size, whereas SSC is an index of cellular complexity, although both parameters can be influenced by other factors.

Preferably, the flow cytometer is equipped with more than one PMT emission detector. The additional PMTs may detect other emission wavelengths, allowing simultaneous detection of more than one fluorochrome, each in individual separate channels. Computers allow the analysis of each channel or the correlation of each parameter with another. Fluorochromes which are typically used with FACS machines include fluorescein isothiocyanate (FITC), which has an emission peak at 525 nm (green), R-phycoerythrin (PE), which has an emission peak at 575 nm (orange-red), propidium iodide (PI), which has an emission peak at 620 nm (red), 7-aminoactinomycin D (7-AAD), which has an emission peak at 660 nm (red), R-phycoerythrin Cy5 (RPE-Cy5), which has an emission peak at 670 nm (red), and allophycocyanin (APC), which has an emission peak at 655-750 nm (deep red).

These and other types of FACS machines may have the additional capability to physically separate the various fractions by deflecting the cells of different properties into different containers.

Any other method for isolating the CD45+ VEGFR+ population of a starting material, such as bone marrow, peripheral blood or cord blood, may also be used in accordance with the present invention. The various subpopulations (e.g., CD14+, Tie2+, CD144−) of the present invention may be isolated in similar manners.

Either before or after the crude cell populations are purified as described above, the population of progenitor cells may be further concentrated by methods known in the art. For example, the progenitor cells can be enriched by positive selection for one or more antigens characteristic of EPCs. Such antigens include, for example, CD14 or Tie-2.

In one embodiment, blood is withdrawn directly from the circulating peripheral blood of a donor. The blood is percolated continuously through a column containing the solid phase-linked binding molecule, such as an antibody VEGFR-2, to capture EPCs. The progenitor cell-depleted blood is returned immediately to the donor's circulatory system by methods known in the art, such as hemapheresis. The blood is processed in this way until a sufficient number of progenitor cells binds to the column. The stem cells are then isolated from the column by methods known in the art. This method allows rare peripheral blood progenitor cells to be harvested from a very large volume of blood, sparing the donor the expense and pain of harvesting bone marrow and the associated risks of anesthesia, analgesia, blood transfusion, and infection.

EPCs are cultivated and proliferated using the methods described herein. Cells are obtained peripheral blood by isolating peripheral blood mononuclear cells (PBMC) by density gradient centrifugation.

Cell suspensions are seeded in any receptacle capable of sustaining cells, particularly culture flasks, culture plates or roller bottles, and more particularly in small culture flasks such as 25 cm 2 culture flasks. Cells cultured in suspension are resuspended at approximately $5 \times 10^4$ to $2 \times 10^5$ cells/ml (for example, $1 \times 10^5$ cells/ml). Cells plated on a fixed substrate arc plated at approximately $2\text{-}3 \times 10^3$ cells/cm$^2$. Optionally, the culture plates are coated with a matrix protein such as collagen. The cells can be placed into any known culture medium capable of supporting cell growth, including HEM, DMEM, RPMI, F-12, and the like, containing supplements which are required for cellular metabolism such as glutamine and other amino acids, vitamins, minerals and proteins such as transferrin and the like. The culture medium may also contain antibiotics to prevent contamination with yeast, bacteria and fungi such as penicillin, streptomycin, gentamicin and the like. The culture medium may contain serum derived from bovine, equine, chicken and the like.

Conditions for culturing should be close to physiological conditions. The pH of the culture medium should be close to physiological pH. (for example, between pH 6-8, between about pH 7 to 7.8, or at pH 7.4). Physiological temperatures range between about 30° C. to 40° C. EPCs are cultured at temperatures between about 32° C. to about 38° C. (for example, between about 35° C. to about 37° C.).

Optionally, the culture medium is supplemented with at least one proliferation-inducing ("mitogenic") growth factor. A "growth factor" is protein, peptide or other molecule having a growth, proliferation-inducing, differentiation-inducing, or trophic effect on EPCs.

"Proliferation-inducing growth factors" are trophic factor that allows EPCs to proliferate, including any molecule that binds to a receptor on the surface of the cell to exert a trophic, or growth-inducing effect on the cell. Proliferation-inducing growth factors include EGF, amphiregulin, acidic fibroblast growth factor (aFGF or FGF-1), basic fibroblast growth factor (bFGF or FGF-2), transforming growth factor alpha (TGFα), VEGF and combinations thereof. Growth factors are usually added to the culture medium at concentrations ranging between about 1 fg/ml to 1 mg/ml. Concentrations between about 1 to 100 ng/ml are usually sufficient. Simple titration assays can easily be performed to determine the optimal concentration of a particular growth factor.

The biological effects of growth and trophic factors are generally mediated through binding to cell surface receptors. The receptors for a number of these factors have been identified and antibodies and molecular probes for specific receptors are available. EPCs can be analyzed for the presence of growth factor receptors at all stages of differentiation. In many cases, the identification of a particular receptor provides guidance for the strategy to use in further differentiating the cells along specific developmental pathways with the addition of exogenous growth or trophic factors.

Generally, after about 3-10 days in vitro, the culture medium of EPCs is replenished by aspirating the medium, and adding fresh medium to the culture flask. Optionally, the aspirated medium is collected, filtered and used as a condition medium to subsequently passage EPCs. For example the 10%, 20%, 30%, 40% or more condition medium is used.

The EPC cell culture can be easily passaged to reinitiate proliferation. For example, after 3-7 days in vitro, the culture flasks are shaken well and EPCs are then transferred to a 50 ml centrifuge tube and centrifuged at low speed. The medium is aspirated, the EPCs are resuspended in a small amount of culture medium The cells are then counted and replated at the desired density to reinitiate proliferation. This procedure can be repeated weekly to result in a logarithmic increase in the number of viable cells at each passage. The procedure is continued until the desired number of EPCs is obtained.

EPCs and EPC progeny can be cryopreserved by any method known in the art until they are needed. (See, e.g., U.S. Pat. No. 5,071,741, PCT International patent applications WO93/14191, WO95/07611, WO96/27287, WO96/29862, and WO98/14058, Karlsson et al., 65 Biophysical J. 2524-2536 (1993)). The EPCs can be suspended in an isotonic solution, preferably a cell culture medium, containing a particular cryopreservant. Such cryopreservants include dimethyl sulfoxide (DMSO), glycerol and the like. These cryopreservants are used at a concentration of 5-15% (for example, 8-10%). Cells are frozen gradually to a temperature of $-10°$ C. to $-150°$ C. (for example, $-20°$ C. to $-100°$ C., or $-70°$ C. to $-80°$ C.).

Treating EPCs with Prostacyclin

According to one aspect of the invention, prostacyclin is used to treat isolated EPCs. The term "prostacyclin" used herein explicitly comprises any prostaglandin $I_2$ ($PGI_2$), any prostacyclin analogues, and any $PGI_2$ receptor agonists. Examples comprise epoprostenol sodium (e.g. Flolan®), treprostinil (e.g. TYVASO®, Remodulin®), ilprost (e.g. Ventavis®), and $PGI_2$ receptor agonist (e.g. Selexipag).

The EPCs treated with prostacyclin exhibit a hyperproliferative phenotype with enhanced angiogenic properties, which are advantageous in treating PAH compared to untreated EPCs.

EPCs can be treated with prostacyclin in various ways. For example, prostacyclin can be used to treat EPCs ex vivo during the expansion of EPCs; prostacyclin can be co-administered with EPCs to the recipient; prostacyclin can also be used to treat EPCs after transplantation. According to one embodiment of the present invention, EPCs are prepared from the recipient's own blood or bone marrow. In that case, prostacyclin can also be used to treat EPCs before they are isolated from the recipients.

Administration of EPCs

Treating PAH by administering/transplanting EPCs arc described in Wang et al., J. Am. Coll. Cardiol. 49:1566-71 (2007), Zhao et al. Circ. Res. 96:442-450 (2005), and Nagaya et al., Circulation 108:889-895(2003), the content of which are hereby incorporated by reference in their entireties.

Administration/Transplantation of EPCs into the damaged blood vessels has the potential to repair damaged vascular tissue, e.g., veins, arteries, capillaries, thereby restoring vascular function. However, the absence of suitable cells for transplantation purposes has prevented the full potential of this procedure from being met. "Suitable" cells are cells that meet one or more of the following criteria: (1) can be obtained in large numbers; (2) can be proliferated in vitro to allow insertion of genetic material, if necessary; (3) capable of surviving indefinitely and facilitate vascular repair on transplantation r; and (4) are non-immunogenic, preferably obtained from a patient's own tissue or from a compatible donor. Suitable EPCs may be autologous, allogeneic or xenogeneic.

EPCs can be administered to a subject with abnormal vasculature or coronary failure symptoms. EPCs can be prepared from the recipient's own blood or bone marrow. In such instances the EPCs can be generated from dissociated tissue and proliferated in vitro using the methods described above. Upon suitable expansion of cell numbers, the EPCs may be harvested, genetically modified if necessary, and readied for direct injection into the recipient's vasculature EPCs can be prepared from donor tissue that is xenogeneic to the host. For xenografts to be successful, some method of reducing or eliminating the immune response to the implanted tissue is usually employed. Thus EPCs recipients can be immunosuppressed, either through the use of immunosuppressive drugs such as cyclosporin, or through local immunosuppression strategies employing locally applied immunosuppressants. Local immunosuppression is disclosed by Gruber, 54 Transplantation 1-11 (1992). U.S. Pat. No. 5,026,365 discloses encapsulation methods suitable for local immunosuppression.

As an alternative to employing immunosuppression techniques, methods of gene replacement or knockout using homologous recombination in embryonic stem cells, taught by Smithies et al., 317 Nature 230-234 (1985), and extended to gene replacement or knockout in cell lines (Zheng et al., 88 Proc. Natl. Acad. Sci. 8067-8071 (1991)), can be applied to EPCs for the ablation of major histocompatibility complex (MHC) genes. EPCs lacking MHC expression allows for the grafting of enriched endothelial cell populations across allogeneic, and perhaps even xenogeneic, histocompatibility barriers without the need to immunosuppress the recipient. General reviews and citations for the use of recombinant methods to reduce antigenicity of donor cells are also disclosed by Gruber, 54 Transplantation 1-11 (1992). Exemplary approaches to the reduction of immunogenicity of transplants by surface modification are disclosed by PCT International patent application WO 92/04033 and PCT/US99/24630. Alternatively the immunogenicity of the graft may be reduced by preparing EPCs from a transgenic animal that has altered or deleted MHC antigens.

EPCs can be encapsulated and used to deliver factors to the host, according to known encapsulation technologies, including microencapsulation (see, e.g., U.S. Pat. Nos. 4,352,883; 4,353,888; and 5,084,350, herein incorporated by reference) and macroencapsulation (see, e.g. U.S. Pat. Nos. 5,284,761, 5,158,881, 4,976,859 and 4,968,733 and PCT International patent applications WO 92/19195 and WO 95/05452, each incorporated herein by reference). Macroencapsulation is described in U.S. Pat. Nos. 5,284,761; 5,158,881; 4,976,859; 4,968,733; 5,800,828 and PCT International patent application WO 95/05452, each incorporated herein by reference. Multiple macroencapsulation devices can be implanted in the host.

EPCs prepared from tissue that is allogeneic to that of the recipient can be tested for use by the well-known methods of tissue typing, to closely match the histocompatibility type of the recipient.

EPCs administered to the vasculature can form a vascular graft, so that the cells form normal connections with neighboring vascular cells, maintaining contact with transplanted or existing endothelial cells. Thus the transplanted EPCs can re-establish the vascular tissue which have been damaged due to disease and aging.

Functional integration of the graft into the host's vascular tissue can be assessed by examining the effectiveness of grafts on restoring various functions.

According to one embodiment of the present invention, EPCs can be co-administered to the recipient with at least one growth factor, such as FGF, VEGF-A, VEGF-B, BMP-4, TGF-Beta, etc. EPCs can also be co-administered to the recipient with mesenchymal stem cells or a culture medium thereof, and/or a prostacyclin (e.g., treprostinil).

Mesenchymal Stem Cells (MSCs)

Mesenchymal stem cells (MSCs) are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into different germ lines such as mesoderm, endoderm and ectoderm. Thus, MSCs are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. MSCs are thus non-hematopoietic progenitor cells which divide to yield daughter cells that are either stem cells or are precursor cells which in time will irreversibly differentiate to yield a phenotypic cell. Examples of MSCs include mesenchymal precursor cells (MPCs).

It is discovered that MSCs can carry out their activities through compounds that can be released into the extracellular environment during growth or differentiation. In some aspects, such compounds include a microvesicle, referred to as exosome, which is between about 30 nm and about 200 nm in diameter. Exosomes can be internalized by host cells in vivo.

Exosomes are vesicles derived from the multivesicular body sorting pathway. Recent studies show that exosomes are bioactive vesicles useful for intercellular communication and facilitation of the immunoregulatory process. MSC exosomes contain 20S proteasomes and numerous RNAs (messenger RNA, non-coding RNA, microRNA).

In addition to exosomes, MSC also release other bioactive molecules/vesicles useful for the purpose of the present disclosure. Such molecules and vesicles include, without limitation, mitochondria and growth factors. Method of preparing culture media that contain such molecules and vesicles released from MSC and further isolating particular molecules and vesicles are known in the art. See, for instance, Hu et al., Frontiers in Genetics, 2:56, 1-9 (2012).

In some embodiments, prior to co-administering a MSC or a MSC-conditioned culture medium with EPC and/or prostacyclin to a patient, the MSC or MSC-conditioned culture medium can be optionally pre-treated with prostacyclin. Accordingly, also provided, in one embodiment, is a method for preparing a mesenchymal stem cell (MSC) or MSC-conditioned culture medium for in vivo delivery, comprising contacting the MSC or MSC-conditioned culture medium with a prostacyclin. Yet another embodiment provides a treated MSC or MSC-conditioned culture medium obtainable by such a method.

Pre-treatment of a cell or a medium with a chemical compound encompasses known techniques. In one aspect, the prostacyclin can be added to and co-incubated with a culture medium that contains a MSC. Optionally, however, such co-incubation can further involve the addition of a growth factor (e.g., VEGF and Angiopoietin-1 or -2, platelet-derived growth factor) and/or hypoxia.

MSCs or MSC-conditioned culture media can be treated with prostacyclin in various ways. For example, prostacyclin can be used to treat MSCs ex vivo during the expansion of MSCs; prostacyclin can also be used to treat MSCs after administration. According to one embodiment of the present disclosure, MSCs can be prepared from the recipient's own blood or bone marrow. In that case, prostacyclin can also be used to treat MSCs before they are isolated from the recipients.

Pharmaceutical Composition

Typically, the cells are administered in a pharmaceutical composition comprising at least one pharmaceutically-acceptable carrier. The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically-acceptable carrier" as used herein means a pharmaceutically-acceptable material, composition or vehicle, such as a liquid or solid filler, diluent, excipient, or solvent encapsulating material.

Pharmaceutically acceptable carriers include saline, aqueous buffer solutions, solvents and/or dispersion media. The use of such carriers are well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

Some examples of materials and solutions which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The pharmaceutical compositions useful for the methods of the invention may comprise a polymeric carrier or extracellular matrix.

A variety of biological or synthetic solid matrix materials (i.e., solid support matrices, biological adhesives or dressings, and biological/medical scaffolds) are suitable for use in this invention. The matrix material is preferably medically acceptable for use in in vivo applications. Non-limiting examples of such medically acceptable and/or biologically or physiologically acceptable or compatible materials include, but are not limited to, solid matrix materials that are absorbable and/or non-absorbable, such as small intestine submucosa (SIS), e.g., porcine-derived (and other SIS sources); crosslinked or non-crosslinked alginate, hydrocolloid, foams, collagen gel, collagen sponge, polyglycolic acid (PGA) mesh, polyglactin (PGL) mesh, fleeces, foam dressing, bioadhesives (e.g., fibrin glue and fibrin gel) and dead de-epidermized skin equivalents in one or more layers.

Suitable polymeric carriers include porous meshes or sponges formed of synthetic or natural polymers, as well as polymer solutions. One form of matrix is a polymeric mesh or sponge; the other is a polymeric hydrogel. Natural polymers that can be used include proteins such as collagen, albumin, and fibrin; and polysaccharides such as alginate and polymers of hyaluronic acid. Synthetic polymers include both biodegradable and non-biodegradable polymers. Examples of biodegradable polymers include polymers of hydroxy acids such as polylactic acid (PLA), polyglycolic acid (PGA), and polylactic acid-glycolic acid (PLGA), polyorthoesters, polyanhydrides, polyphosphazenes, and combinations thereof. Non-biodegradable polymers include polyacrylates, polymethacrylates, ethylene vinyl acetate, and polyvinyl alcohols.

Polymers that can form ionic or covalently crosslinked hydrogels which are malleable are used to encapsulate cells. A hydrogel is a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked ionically, or block copolymers such as Pluronics™ or Tetronics™, polyethylene oxide-polypropylene glycol block copolymers which are crosslinked by temperature or pH, respectively. Other materials include proteins such as fibrin, polymers such as polyvinylpyrrolidone, hyaluronic acid and collagen.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups. Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Further, a composition used for a method of the invention may comprise at least one therapeutic agent. For example, the composition may contain an analgesic to aid in treating inflammation or pain, or an anti-infective agent to prevent infection of the site treated with the composition. More specifically, non-limiting examples of useful therapeutic agents include the following therapeutic categories: analgesics, such as nonsteroidal anti-inflammatory drugs, opiate agonists and salicylates; anti-infective agents, such as antihelmintics, antianaerobics, antibiotics, aminoglycoside antibiotics, antifungal antibiotics, cephalosporin antibiotics, macrolide antibiotics, miscellaneous .beta.-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, anti-inflammatory agents, corticosteroid anti-inflammatory agents, antipruritics/local anesthetics, topical anti-infectives, antifungal topical anti-infectives, antiviral topical anti-infectives; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, gastrointestinal anti-inflammatory agents, gastrointestinal anti-inflammatory agents, antacid anti-ulcer agents, gastric acid-pump inhibitor anti-ulcer agents, gastric mucosal anti-ulcer agents, H2-blocker anti-ulcer agents, cholelitholytic agent's, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hormones and hormone modifiers, such as abortifacients, adrenal agents, corticosteroid adrenal agents, androgens, anti-androgens, immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immunosuppressive anti-inflammatory agents, nonsteroidal anti-inflammatory drugs (NSAIDs), salicylate anti-inflammatory agents, minerals; and vitamins, such as vitamin A, vitamin B, vitamin C, vitamin D, vitamin E, and vitamin K.

Compositions useful for the methods of the present invention may include cell culture components, e.g., culture media including amino acids, metals, coenzyme factors, as well as small populations of other cells, e.g., some of which may arise by subsequent differentiation of the stem cells.

Compositions useful for the methods of the present invention may be prepared, for example, by sedimenting out the subject cells from the culture medium and re-suspending them in the desired solution or material. The cells may be sedimented and/or changed out of the culture medium, for example, by centrifugation, filtration, ultrafiltration, etc.

The skilled artisan can readily determine the amount of cells and optional carrier(s) in compositions and to be administered in methods of the invention. In an embodiment, any additives (in addition to the active cell(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and LD50 in a suitable animal model e.g., rodent such as mouse; and, the dosage of the composition(s), concentration of components therein and timing of administering the composition (s), which elicit a suitable response. Such determinations do not require undue experimentation from the knowledge of the skilled artisan, this disclosure and the documents cited herein. And, the time for sequential administrations can be ascertained without undue experimentation.

Compositions useful for the methods of the present invention can be administered via, inter alia, localized injection, including catheter administration, systemic injection, localized injection, intravenous injection, intrauterine injection or parenteral administration. When administering a therapeutic composition described herein (e.g., a pharmaceutical com- Genetic Modification of EPCs In one embodiment, the cells used in the methods of the invention are genetically modified. Preferably, the cells are genetically modified to produce a heterologous protein. Typically, the cells will be genetically modified such that the heterologous protein is secreted from the cells. However, in an embodiment the cells can be modified to express a functional non-protein encoding polynucleotide such as dsRNA (typically for RNA silencing), an antisense oligonucleotide or a catalytic nucleic acid (such as a ribozyme or DNAzyme). In one embodiment, the EPC is genetically modified to express or overexpress a protein selected from the group consisting of endothelial nitric oxide synthase (eNOS), heme oxygenase (HMOX1) and prostacyclin synthase (PTGIS).

Genetically modified cells may be cultured in the presence of at least one cytokine in an amount sufficient to support growth of the modified cells. The genetically modified cells thus obtained may be used immediately (e.g., in transplant), cultured and expanded in vitro, or stored for later uses. The modified cells may be stored by methods well known in the art, e.g., frozen in liquid nitrogen.

Genetic modification as used herein encompasses any genetic modification method which involves introduction of an exogenous or foreign polynucleotide into a cell described herein or modification of an endogenous gene within the cell. Genetic modification includes but is not limited to transduction (viral mediated transfer of host DNA from a host or donor to a recipient, either in vitro or in vivo), transfection (transformation of cells with isolated viral DNA genomes), liposome mediated transfer, electroporation, calcium phosphate transfection or coprecipitation and others. Methods of transduction include direct co-culture of cells with producer cells or culturing with viral supernatant alone with or without appropriate growth factors and polycations.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method for treatment pulmonary hypertension, comprising administering to a subject suffering from pulmonary hypertension (i) a first prostacyclin and (ii) microvesicles obtained from mesenchymal stem cells (MSCs) contacted with a second prostacyclin prior to administration.

2. The method of claim 1, wherein the first and second prostacyclin are the same prostacyclin.

3. The method of claim 1, wherein the first or second prostacyclin is treprostinil.

4. The method of claim 1, wherein the first prostacyclin and microvesicles are co-administered.

5. The method of claim 1, wherein the first prostacyclin is administered before the microvesicles are administered.

6. The method of claim 1, wherein the first prostacyclin is administered after the microvesicles are administered.

7. The method of claim 1, wherein the microvesicles are isolated from a culture medium comprising the MSCs.

8. The method of claim 1, further comprising administering to the subject the MSCs.

9. The method of claim 1, further comprising administering to the subject endothelial progenitor cells (EPCs).

10. The method of claim 1, wherein the patient is suffering from pulmonary arterial hypertension.

11. A method for treating pulmonary arterial hypertension comprising:
(a) providing isolated endothelial progenitor cells (EPCs);
(b) treating the isolated EPCs in vitro or ex vivo with a prostacyclin during expansion of the EPCs, wherein the treated EPCs exhibit a hyperproliferative phenotype with enhanced angiogenic activity; and
(c) administering a composition comprising the treated EPCs to a human subject suffering from pulmonary hypertension.

12. The method of claim 11, wherein the EPCs are isolated from a human being, a tissue, or cell culture.

* * * * *